United States Patent
Nabutovsky et al.

(10) Patent No.: US 8,175,668 B1
(45) Date of Patent: May 8, 2012

(54) IMPLANTABLE MULTI-WAVELENGTH VENOUS OXYGEN SATURATION AND HEMATOCRIT SENSOR AND METHOD

(75) Inventors: Yelena Nabutovsky, Mountain View, CA (US); Gene A. Bornzin, Simi Valley, CA (US); Taraneh Ghaffari Farazi, San Jose, CA (US); John W. Poore, South Pasadena, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1232 days.

(21) Appl. No.: 11/877,056

(22) Filed: Oct. 23, 2007

(51) Int. Cl.
*A61B 5/1455* (2006.01)

(52) U.S. Cl. .................. 600/323; 600/326; 600/327

(58) Field of Classification Search .......... 600/310, 600/322–328, 331–333, 342; 356/39–41; 702/19
See application file for complete search history.

(56) References Cited

U.S. PATENT DOCUMENTS

| | | | |
|---|---|---|---|
| 4,114,604 A | 9/1978 | Shaw et al. | |
| 4,623,248 A * | 11/1986 | Sperinde | 600/342 |
| 4,776,340 A | 10/1988 | Moran et al. | |
| 4,809,697 A | 3/1989 | Causey, III et al. | |
| 4,944,299 A | 7/1990 | Silvian | |
| 5,048,524 A | 9/1991 | Bailey | |
| 5,061,632 A | 10/1991 | Shepherd et al. | |
| 5,149,503 A | 9/1992 | Kohno et al. | |
| 5,282,466 A * | 2/1994 | Duffy et al. | 600/323 |
| 6,064,474 A | 5/2000 | Lee et al. | |
| 6,103,197 A | 8/2000 | Werner | |
| 6,144,444 A | 11/2000 | Haworth et al. | |
| 6,181,958 B1 | 1/2001 | Steuer et al. | |
| 6,275,734 B1 | 8/2001 | McClure et al. | |
| 6,711,425 B1 | 3/2004 | Reuss | |
| 6,714,805 B2 | 3/2004 | Jeon et al. | |
| 7,029,628 B2 | 4/2006 | Tam et al. | |

OTHER PUBLICATIONS

Bornzin et al., entitled "Measuring Oxygen Saturation and Hematocrit Using a Fiberoptic Catheter", IEEE/9th Annual Conf. of the Eng. & Biol. Soc. (1987).
Steinke et al., "Reflectance Measurements of Hematocrit and Oxyhemoglobin Saturation," Am J Circ Physiol 253: H147-H153 (1987).

* cited by examiner

*Primary Examiner* — Eric Winakur
*Assistant Examiner* — Chu Chuan Liu
(74) *Attorney, Agent, or Firm* — Steven M. Mitchell

(57) ABSTRACT

An intravenous implantable optical sensor assesses the relative absorbance of multiple wavelengths of light in order to determine oxygen saturation. The calculation of oxygen saturation is enhanced by use of a function of hematocrit which is derived from the relative absorbance of light of an isobestic wavelength along two different length paths through the blood. The use of the hematocrit-dependent term and multiple wavelengths of light to calculate oxygen saturation provides results that are less susceptible to noise and variation in hematocrit and thus provides a more accurate measure of oxygen saturation over a wider range of conditions than previously possible. The optical sensor may form part of an implantable system which performs the calculation of oxygen saturation and uses the results for a diagnostic or therapeutic purpose.

24 Claims, 9 Drawing Sheets

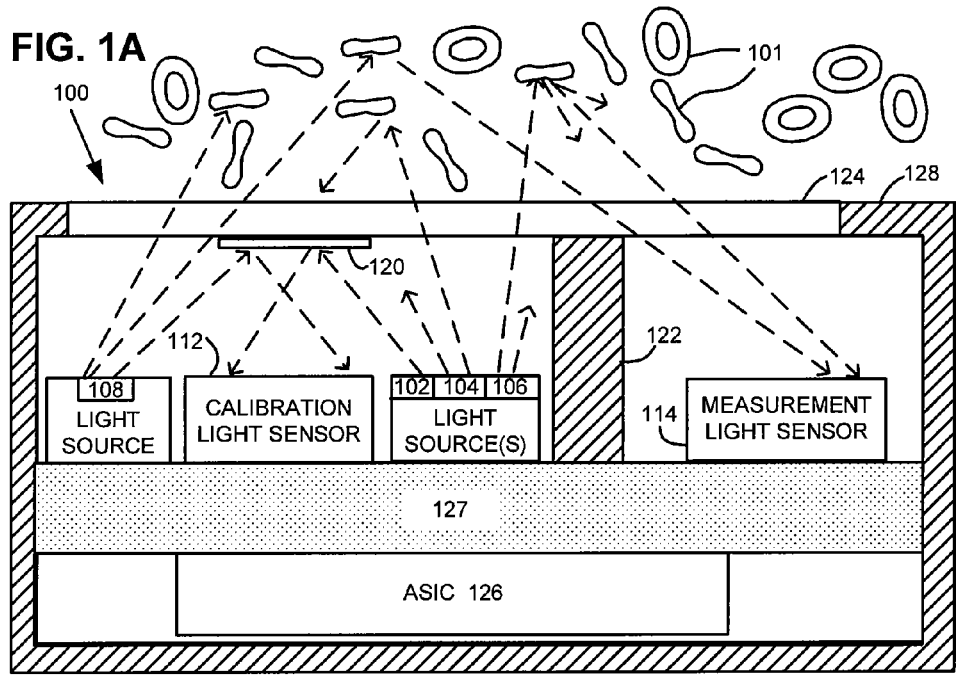
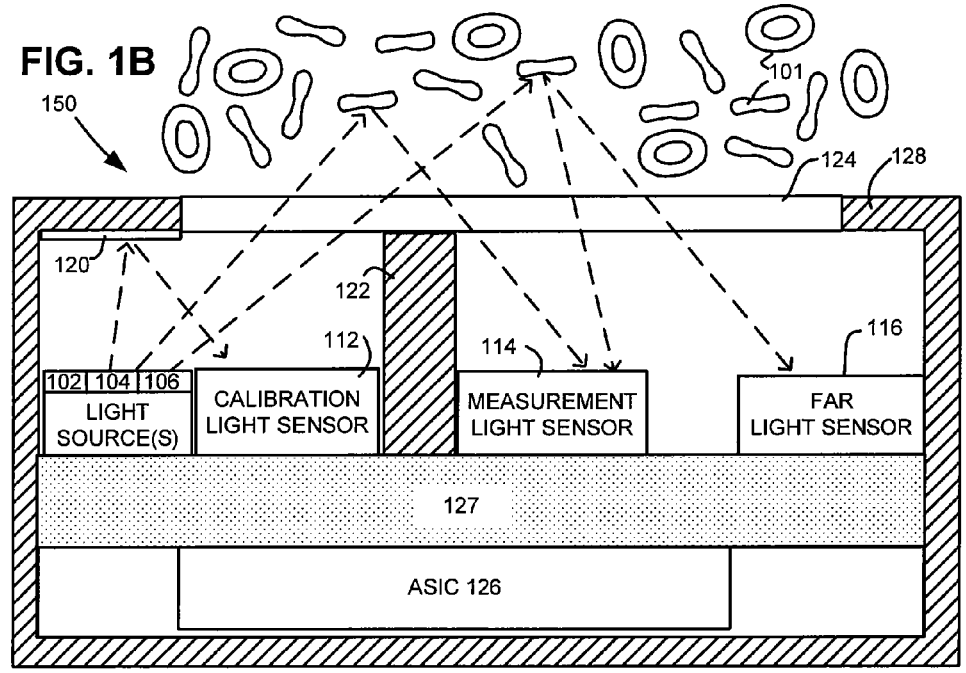

FIG. 5A
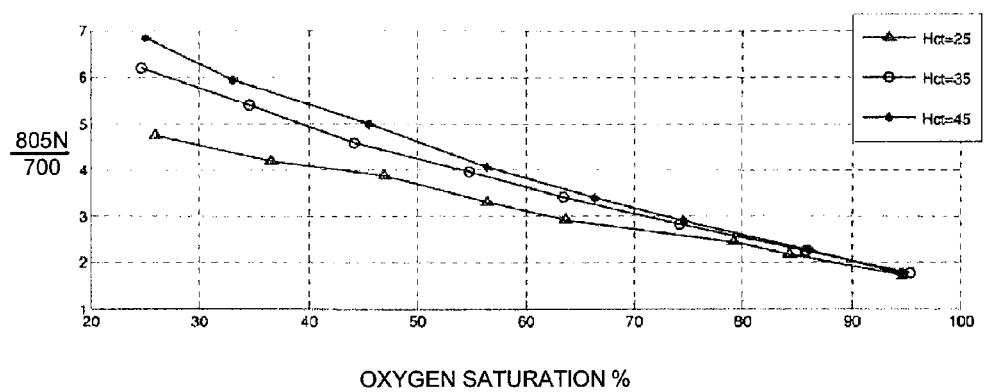
OXYGEN SATURATION %
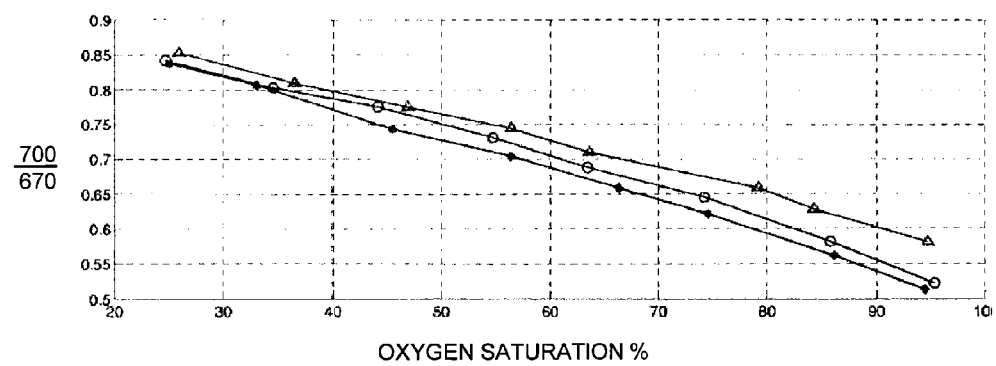
OXYGEN SATURATION %
FIG. 5B

IMPLANTABLE MULTI-WAVELENGTH VENOUS OXYGEN SATURATION AND HEMATOCRIT SENSOR AND METHOD

FIELD OF THE INVENTION

Embodiments of the present invention relate to implantable self-calibrating optical sensors that are used, e.g., for obtaining measures of blood oxygen saturation and/or hematocrit.

BACKGROUND

Blood oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. When radiant energy (e.g., light) is incident upon red blood cells, the red blood cells both reflect and absorb the incident radiant energy. Oxygenated and non-oxygenated hemoglobin reflect and absorb the radiant energy incident on the red blood cells differently. Thus, oxygen saturation may be determined by analyzing the radiant energy scattered back from the red blood cells.

An oxymetry sensor can use radiant energy of one, two or more different centered wavelengths to obtain measures of blood oxygen saturation. The oxymetry sensor emits radiant energy of a particular wavelength into the blood and measures the radiant energy scattered back from the blood. For a given (non-isobestic) wavelength, the intensity of light scattered back by the blood varies based on the relative concentrations of hemoglobin and oxyhemoglobin. Because the relationship between scattering and oxygen saturation is known, the oxygen saturation can be calculated from the measured light intensity. However, single wavelength oxymetry systems are highly susceptible to noise and can only be used to measure relative changes in oxygen saturation.

Many sources of noise have the same effect upon different wavelengths of light and thus by looking at relative light scattering instead of absolute light scattering, the effects of many sources of noise can be eliminated. Thus, multi-wavelength oxymetry systems are less susceptible to noise and can be used to generate absolute measures of oxygen saturation. However, one problem with multi-wavelength oxymetry sensors is that the relationship between scattering and oxygen saturation is different for each different wavelength. Furthermore, the relationship between scattering and oxygen saturation is different for different wavelengths and different hematocrit. Thus, even in multi-wavelength oxymetry systems, the accuracy of the oxymetry system can vary over the range of hematocrit and oxygen saturation conditions which the oxymetry system may encounter.

In view of the disadvantages of the state of the art with respect to oxygen saturation, it would be desirable to have a multi-wavelength oxymetry system that achieves as accurate a reading of oxygen saturation as possible over a large range of possible conditions.

It would also be desirable to have a multi-wavelength oxymetry system that compensates for changes in oxygen saturation and hematocrit to ensure that oxygen saturation is measured accurately over a large range of possible conditions.

SUMMARY OF THE INVENTION

In view of the background above and disadvantages of the state of the art, the present invention provides, in a general embodiment implantable multi-wavelength oxymetry systems, and methods for use therewith, that achieve an accurate measurement of oxygen saturation over a large range of possible conditions. In a general embodiment the oxymetry system compensates for changes in oxygen saturation and hematocrit to ensure that the oxygen saturation is measured accurately over a large range of possible conditions. The oxymetry system combines a plurality of absorption and/or scattering measurements obtained for different wavelengths of light and calculates the oxygen saturation as a function of the relative reflectance of the blood for two or more different wavelengths of light in combination with a hematocrit-dependent term.

In accordance with a specific embodiment of the present invention, an implantable oxymetry system includes an oxymetry sensor which comprises an implantable housing including a window through which light can pass. Included within the housing are a plurality of light sources, a measurement light sensor and a calibration light sensor. Each light source transmits light of a single wavelength. A portion of the light of each wavelength exits the housing through the window. An opaque barrier between the light sources and the measurement light sensor blocks most light from traveling directly from the light source to the measurement light sensor without passing through the blood. The measurement light sensor detects light of each wavelength scattered back into the housing through the window, and produces a measurement signal that is indicative of the intensity of the light of each wavelength detected by the measurement light sensor. A processor calculates ratios of the measurement signals for the plurality of wavelengths of light to determine oxygen saturation and hematocrit. Oxygen saturation is calculated using equations which are corrected based on hematocrit to improve the accuracy of the oxygen saturation calculation.

In accordance with another specific embodiment of the present invention, the implantable oxymetry system comprises part of an implantable stimulation device. Connected with the implantable stimulation device are a plurality of light sources and a measurement light sensor. Each light source transmits light of a single wavelength. A portion of the light of each wavelength exits the housing through the window. The measurement light sensor detects light of each wavelength scattered back into the housing through the window, and produces a measurement signal that is indicative of the intensity of the light of each wavelength detected by the measurement light sensor. An optional calibration light sensor, if provided, can measure the output of each light sensor in order to control for variations in light intensity output. A processor within the implantable stimulation device calculates ratios of the measurement signals for the plurality of wavelengths of light to determine oxygen saturation and hematocrit. Oxygen saturation is calculated using equations which are corrected based on a hematocrit-dependent term to improve the accuracy of the oxygen saturation calculation.

This summary is not intended to be a complete description of the invention. Other features, aspects, objects and advantages of the invention can be obtained from a review of the specification, the figures, and the claims.

BRIEF DISCRIPTION OF THE DRAWINGS

FIG. 1A illustrates a schematic sectional diagram of an implantable oximetry sensor, according to one embodiment of the present invention.

FIG. 1B illustrates a schematic sectional diagram of an implantable oximetry sensor, according to another embodiment of the present invention.

FIG. 5A is a graph of a first light intensity ratio against oxygen saturation for different levels of hematocrit.

FIG. 5B is a graph of a second light intensity ratio against oxygen saturation for different levels of hematocrit.

Figure 8:
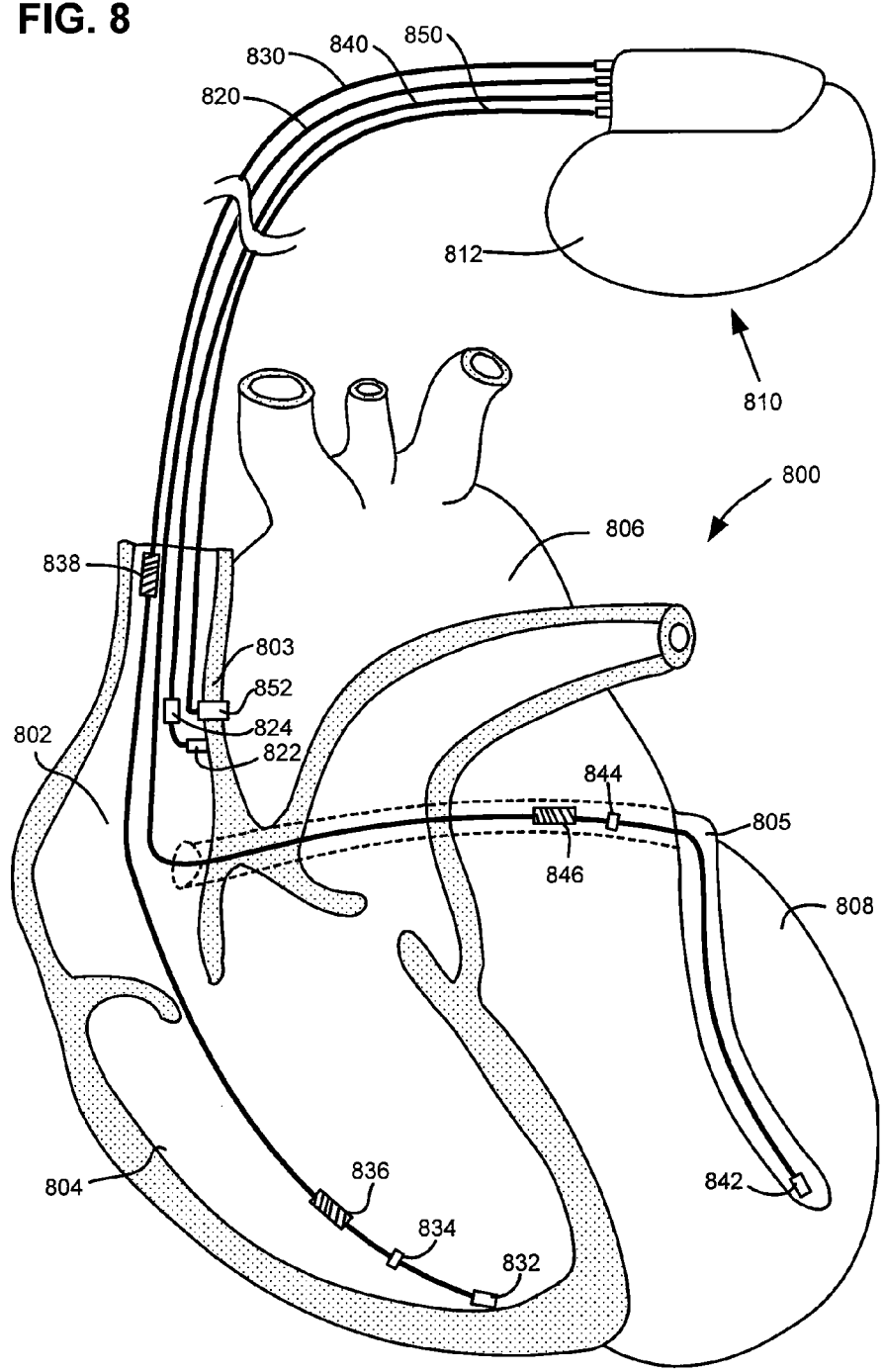
FIG. 8 illustrates an implantable stimulation device in electrical communication with the heart and comprising an implantable oxymetry system in accordance with one embodiment of the present invention.
Figure 9:
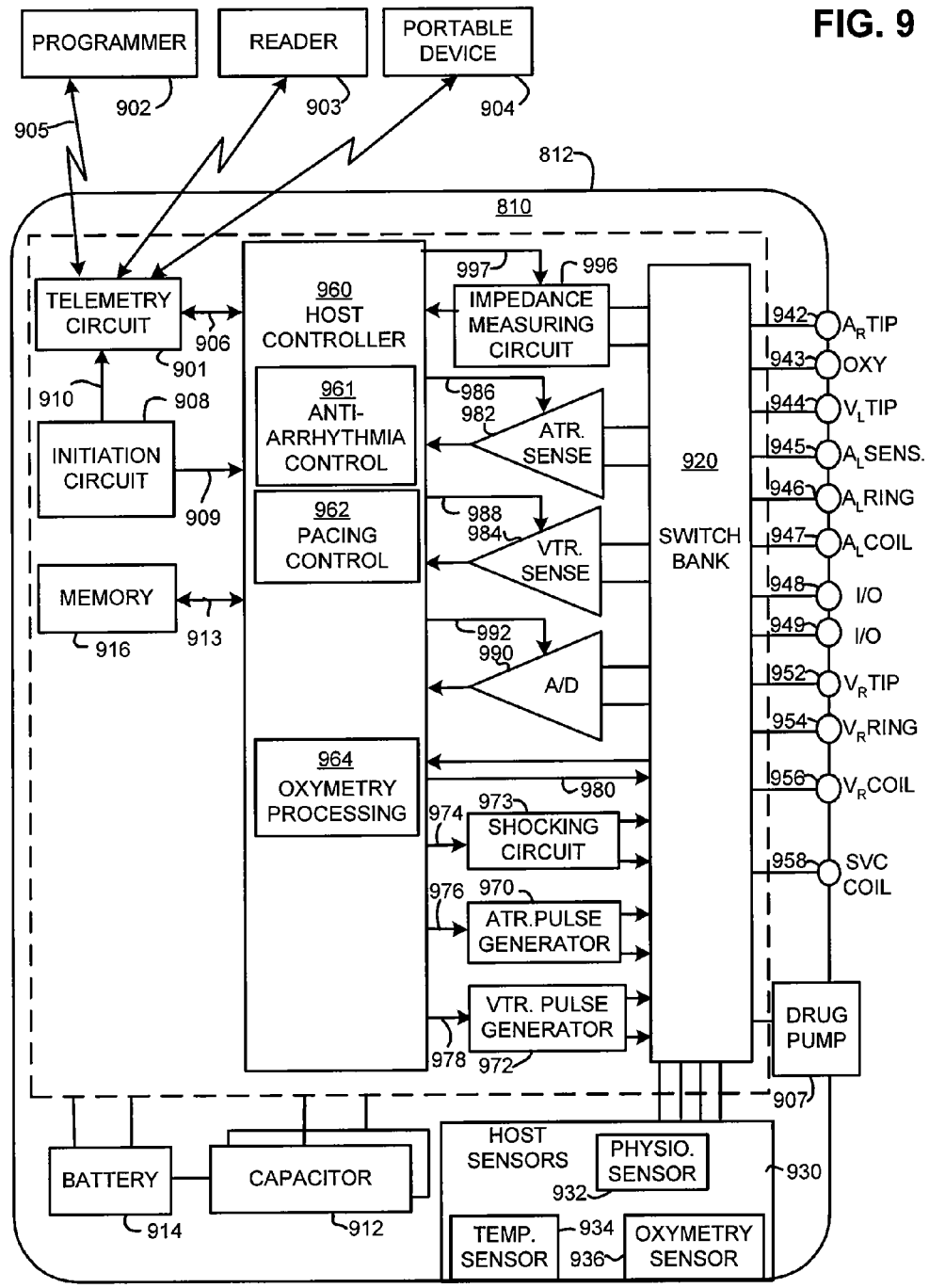

FIG. 9 illustrates a functional block diagram of the multi-chamber implantable stimulation device of FIG. 8, illustrating the basic elements that provide cardioversion, defibrillation and/or pacing stimulation in four chambers of the heart and illustrating a blood-oxygen saturation and hematocrit monitoring unit for automatically calculating blood-oxygen saturation from oxymetry sensor measurements in accordance with one embodiment of the present invention.

DETAILED DESCRIPTION OF THE INVENTION

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit of a reference number identifies the drawing in which the reference number first appears.

Oxymetry Sensors

Referring now to FIG. 1A, there is shown an exemplary oxymetry sensor 100 suitable for use in an embodiment of the present invention. Oxymetry sensor 100 uses light sources of three different-centered wavelengths to obtain measures of blood-oxygen saturation. Oxymetry sensor 100 emits light into the blood. The absorption and/or scattering of the light by the blood is measured using a measurement light sensor 114 which detects light scattered back from the blood. The light measured by the measurement light sensor 114 allows for the calculation of the relative concentration of reduced hemoglobin and oxyhemoglobin, and therefore blood-oxygen saturation levels, since the absorption and/or scattering relationships are known.

Implantable oxymetry sensor 100 includes an implantable housing 128 including a window 124 through which light can pass to fall on red blood cells 101. The term window, as used herein, is intended to collectively encompass all portions of the housing through which light of interest can enter and exit the housing, even if such portions are separated from one another (e.g., by opaque portions). Included within the housing are three light sources 102, 104, 106, one far light source 108, the measurement light sensor 114 and a calibration light sensor 112. Light sources 102, 104, 106 transmit light at wavelengths 670 nm, 705 nm, and 805 nm respectively. Far light source 108 transmits light at a wavelength of 805 nm (which is an isobestic wavelength). The light sources 102, 104, 106, 108 are separated from measurement light sensor 114 by a barrier 122 that obstructs light from traveling directly to the measurement light sensor 114 from the light sources without passing through the blood.

A reflective surface 120 is provided to reflect some but not all of the light emitted by light sources 102, 104, 106 and 108 onto the calibration light sensor 112. The calibration light sensor 112 detects and measures light of each wavelength reflected back by the reflective surface 120. The measurement light sensor 114 detects and measures light of each wavelength scattered back by blood cells 101 into the housing through the window 124. The signal from the calibration sensor can be used to normalize the intensity of the light emitted by the light sources or the output of the measurement light sensor as described with respect to FIG. 3, below. The intensity of the light transmitted by each light source is controlled by ASIC 126. In operation, ASIC 126 causes each light source to be activated in turn and receives the intensity measurement with respect to that light source from calibration light sensor 112 and measurement light sensor 114.

FIG. 1B illustrates a different embodiment of an oxymetry sensor 150 suitable for use in the present invention. Oxymetry sensor 150 has the same components as oxymetry sensor 100 with the exception that, oxymetry sensor 150 does not have a far light source 108. Oxymetry sensor 150 is instead provided with an additional light sensor, far light sensor 116. The far light sensor 116 provides the same functionality because it allows a comparison of the intensity of 805 nm light scattered back along a long path as compared to a short path through the blood. However, using a pair of spatially separated 805 nm light sources is advantageous, as compared to using a pair of spatially separated measurement light sensors, because light sources (such as LEDs) are typically significantly smaller than photodetectors, thus resulting in space savings.

Figure 2A:
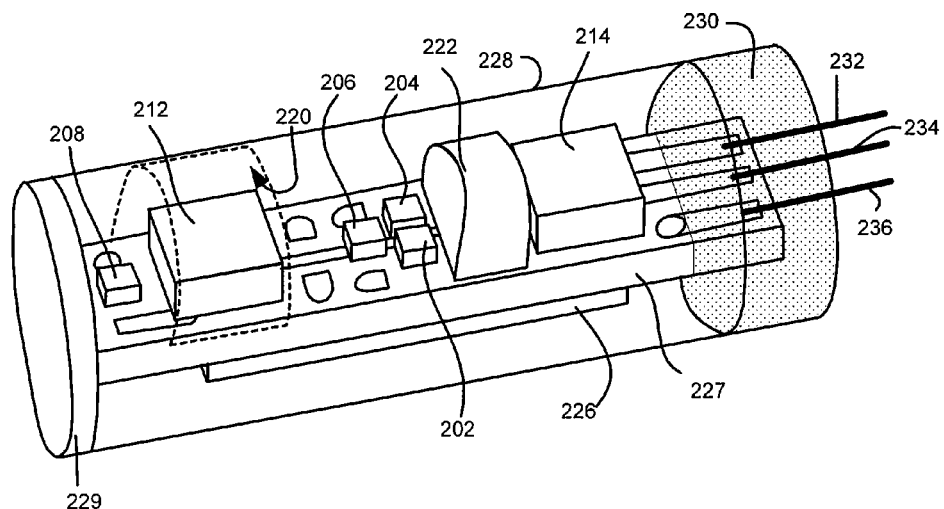
FIG. 2A illustrates a perspective view of an implantable lead that includes the sensor of FIG. 1A.

FIG. 2A illustrates a perspective view of the oxymetry sensor of FIG. 1A, in accordance with an embodiment of the present invention. FIG. 2A illustrates the physical arrangement of the components of the oxymetry sensor. In accordance with an embodiment of the present invention, housing 128 comprises a tube 228 and an end cap 229. The components of the oxymetry sensor are hermetically sealed within the housing 128 by an epoxy plug 230. The tube 228 can be made of an opaque material, such as metal (e.g., titanium or stainless steel) or ceramic, so long as it includes a window that passes light of all the wavelengths of interest. The window can for example be made of synthetic sapphire or some other appropriate material that passes light of all the wavelengths of interest. However, as shown in FIG. 2A, the entire tube 228 can be made of a material that passes light of all the wavelengths of interest, and thus, in this embodiment the entire tube 228 can be considered a window. The entire tube 228 can, for example, be made of synthetic sapphire. Exemplary synthetic sapphire windows and tubes are marketed by Imetra, Inc. (Elmsford, N.Y.) and Swiss Jewel (Philadelphia, Pa.).

Figure 2B:
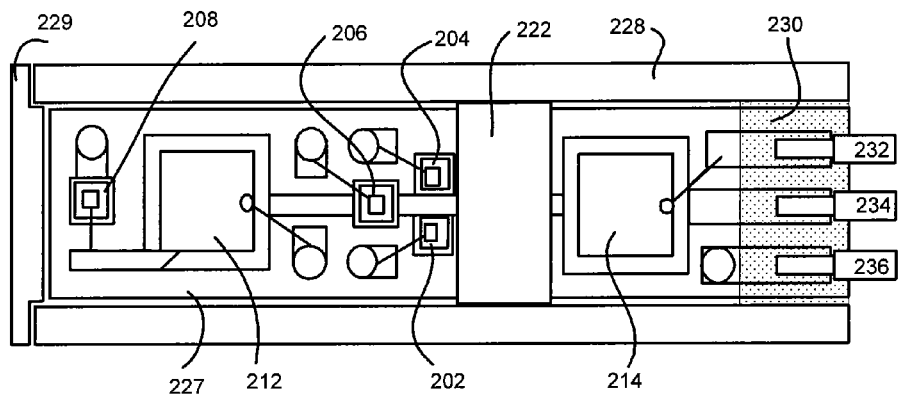
FIG. 2B illustrates a plan view of an implantable lead that includes the oxymetry sensor of FIG. 1A.

Referring again to FIG. 2A light sources 202, 204, 206, 208 are shown on substrate 227. The light sources may be attached to the substrate by epoxy or similar adhesives. In a preferred embodiment, light sources, 202 and 208 comprise 805 nm LEDs and light sources 204 and 206 comprise 670 nm and 700 nm LEDs respectively although LEDS of different wavelengths may be used without departing from the scope of the invention. Measurement light sensor 214 and calibration light sensor 212 comprise photodiodes and are likewise attached to substrate 227. An opaque optical wall 222 is positioned between the light sources and the measurement light sensor 214. A reflective surface 220 is provided on the inside of sapphire tube 228 in order to reflect a portion of the light emitted by the light sources 202, 204, 206, 208 onto calibration light sensor 212. Substrate 227 comprises a printed wire board that, in addition to supporting the components of the oxymetry sensor, also provides electrical connections between the LEDs 202, 204, 206 and 208, photodiodes 212 and 214, and ASIC 226 which is located on the opposite side of substrate 227. Power is transmitted to oxymetry sensor 200 and data transmitted from oxymetry sensor 200 through a number of conductive leads 232, 234 and 236 that pass through epoxy plug 230 and connect to substrate 227. FIG. 2B illustrates a plan view of the oxymetry sensor of FIG. 2A illustrating the positions of the components on substrate 227.

Referring again to FIG. 2A, in accordance with specific embodiments of the present invention, the oxymetry sensor 200 is built into an implantable lead. Accordingly, in this embodiment, the housing 228 of the oxymetry sensor 200 is sized to fit within the implantable lead. More specifically, the diameter of the oxymetry sensor 200 is about 4 mm or less, and preferably about 3 mm. The length of the oxymetry sensor 200, which extends axially in the lead, can be somewhat larger, because the length of the lead is relatively large as compared to the diameter of the lead. However, the sensor should be small enough in length and diameter that the implantation of the lead into the desired location with a patient is not impaired. Further, the portion of the lead that is adjacent to where light is to exit and enter, should allow the light to pass in and out of the oxymetry sensor 100. Thus, the lead may be transparent, or include its own window, opening, or the like. More detailed descriptions of oxymetry sensors suitable for use in the present invention may be found in copending patent application U.S. Ser. No. 11/282,198 filed Nov. 17, 2005 entitled "Implantable Self Calibrating Optical Sensors" and invented by John W. Poore, which is incorporated herein by reference.

Figure 3:
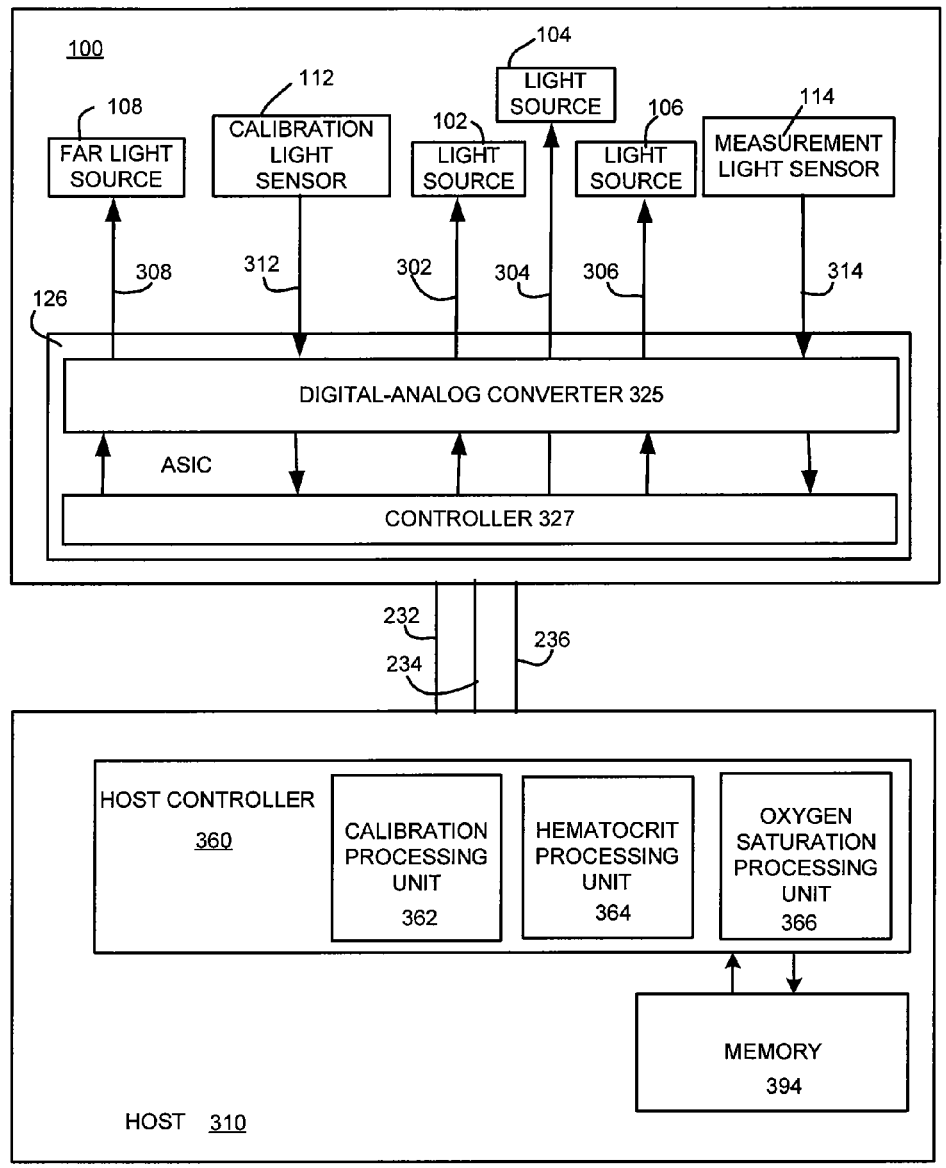
FIG. 3 illustrates a schematic diagram of an oxymetry system incorporating the oxymetry sensor of FIG. 1A.

FIG. 3 illustrates a schematic diagram of the circuitry of the oxymetry sensor 100 of FIG. 1A. As shown in FIG. 3, ASIC 126 comprises digital to analog conversion circuitry 325 which comprises a plurality of digital to analog and analog to digital circuits. ASIC 126 also comprises a controller 327. Note that circuitry 325 provides analog drive signals 302, 304, 306, 308 to drive light sources 102, 104, 106 and far light source 108. Each light source transmits light having an intensity that is controlled by the corresponding drive signal, which is typically a current signal, but can be a voltage signal. Each drive signal is controlled by controller 327, which outputs a digital drive control signal which is converted to a corresponding analog drive signal by digital-to-analog converter 325. The controller 327 in this embodiment, and other embodiments, can be a microcontroller, a processor, a state machine, random logic, or the like. In practice, the light sources 102, 104, 106 and 108 are serially energized, in a non-overlapping temporal relationship. This allows separate measurements of the intensity of light received from each light source by calibration light sensor 112 and measurement light sensor 114.

When transmitted toward patient tissue, some of the light energy is scattered by the blood. The different wavelengths are scattered differently depending on the oxygen saturation level of the blood. Measurement light sensor 114 receives light from each of the light sources 102, 104, 106, 108 and generates an analog measurement signal 314 indicative of the intensity of light received from the active light source. At a high level, time multiplexing is used to produce a signal path for each of the different wavelengths of received light. Each signal path will typically include one or more filters and an ND converter to sample the received light signals. The analog measurement signal is converted by circuitry 325 into a digital measurement signal indicative of the intensity of light received from each light source and provided to controller 327. Controller 327 delivers signals indicative of the intensity of the light detected from each source to host controller 360. Using electronic circuitry, firmware and/or software, the received light signals can be analyzed by controller 360 so that oxygen saturation levels can be determined according to the methods described below for diagnostic and/or therapeutic use.

As the light sources age they may become less efficient in that for a same drive signal they will transmit light of less intensity. If not compensated for, this will affect the intensity of the light detected by the measurement light sensor 114 which will in turn adversely effect determinations of blood oxygen saturation. In accordance with specific embodiments of the present invention, calibration light sensor 112 is added, the output of which is used to compensate for aging or other changes to the light source(s). In accordance with specific embodiments, the controller 327 adjusts drive signals 302, 304, 306, 308 based on the calibration signal 312, to keep the intensity of the light transmitted by each light source substantially constant. In accordance with other embodiments of the present invention, controller 327 adjusts the measurement signal 314, based on the calibration signal 312, to compensate for changes in the intensity of the light transmitted by each light source 102, 104, 106, 108. In still other embodiments, rather than adjusting the drive signals or measurement signals, controller 327 provides an additional calibration signal to the host controller 360 which calculates the oxygen saturation and hematocrit. The host controller 360 comprises a calibration processing unit 362 which may in some embodiments take into account the changes in intensity when using the measurement signal 314 for a diagnostic and/or therapeutic purpose. For example, the host controller 360 can take changes in intensity into account by making appropriate adjustments to algorithms that are used to determine levels of blood-oxygen saturation and/or levels of hematocrit based on the measurement signal 314. Host controller 360 further comprises a hematocrit processing unit 364 and an oxygen saturation processing unit 366 which can calculate hematocrit and oxygen saturation as described below.

Calculation of Hematocrit

Hematocrit is a measure of the proportion of blood volume that is occupied by red blood cells. It is normally between 0.42 and 0.52 for men and between 0.36 and 0.48 for women. Various techniques are known for determining hematocrit based on scattered light. For example, light of about 500 nm and light of about 800 nm can be directed at a blood sample, and an algorithm can be used to calculate hematocrit based on the relative intensities of detected scattered light. In another technique, a pair of spatially-separated photodetectors can be used to detect reflected infra red (IR) light, e.g., of 805 nm. The intensity of the IR light detected by the photodetector that is nearer to the IR light source is referred to as IRnear, and the intensity of the IR light detected by the photodetector farther from the IR light source is referred to as IRfar. As described in an article by Bornzin et al., entitled "Measuring Oxygen Saturation and Hematocrit Using a Fiberoptic Catheter", *IEEE/9th Annual Conf of the Eng. & Biol. Soc.* (1987), which is incorporated herein by reference, the ratio: Rh=IRnear/

IRfar is directly related to hematocrit. Note that, as used herein, a "ratio" is a value calculated by dividing one number by another. For example, if IRnear is 2 and IRfar is 4, Rh is 0.5. The ratio Rh is also relatively independent of oxygen saturation because 805 nm is a wavelength that is absorbed equally by oxyhemoglobin and deoxyhemoglobin, i.e. an isobestic wavelength.

In one embodiment, two light sources (e.g., two 805 nm LEDs) can be spatially separated and time multiplexed, with one light source being closer to the measurement light sensor 114 than the other. In an alternative embodiment, the same ratio, Rh=IRnear/IRfar can be determined, with IRnear corresponding to scattered light originating from an LED detected by a close photodetector, and IRfar corresponding to scattered light originated from the same LED but detected by a more distant measurement photodetector 806. Embodiments of oxymetery sensors suitable for measuring hematocrit are shown in FIGS. 1A, 1B, 2A, 2B and 3 described above.

Figure 4A:
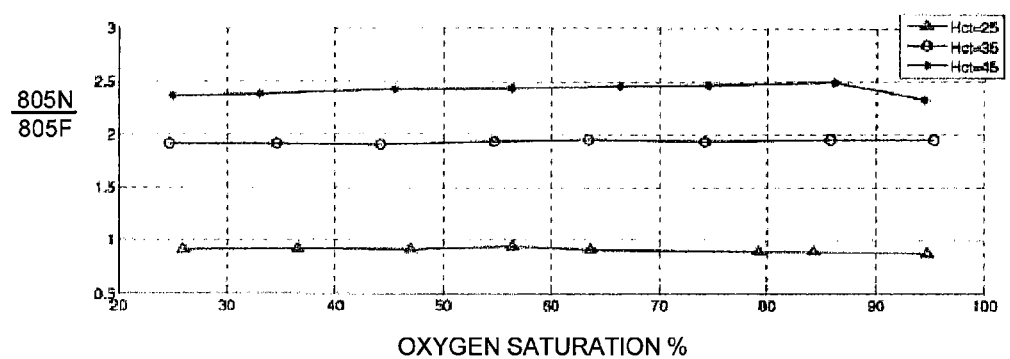
FIG. 4A is a graph of a light intensity ratio against oxygen saturation for different levels of hematocrit using two isobestic light sources.
Figure 4B:
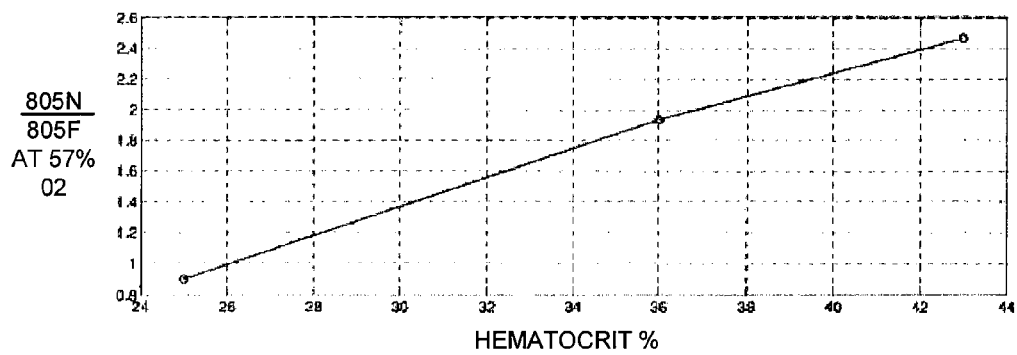
FIG. 4B illustrates a graph of the light intensity ratio against hematocrit at a fixed oxygen saturation.

Host controller 360 comprises hematocrit processing unit 364 for determining the hematocrit from measurement signal 314. The oxymetry sensor 100 provides four intensity signals, one for each light source, to oxygen saturation processing unit 366. The intensity signals are $\lambda_1$, $\lambda_2$, $\lambda_3$ and $\lambda_{3\text{-far}}$) where $\lambda_3$ is the intensity signal from the 805 nm light source located near the measurement light sensor 114 and $\lambda_{3\text{-far}}$ is the intensity signal from the far 805 nm light source. The $\lambda_3$ and $\lambda_{3\text{-far}}$ signals can be used to generate the ratio Rh. FIGS. 4A, 4B illustrate experimentally-obtained results for the ratio, Rh, of $\lambda_3/\lambda_{3\text{-far}}$. Note that, as shown in FIG. 4A, Rh does not vary significantly over a wide range of oxygen saturation. This is to be expected because 805 nm is an isobestic wavelength which is absorbed/scattered equally by oxygenated and deoxygenated hemoglobin. However, as shown in FIG. 4B, Rh has an almost linear relationship to hematocrit. The greater the hematocrit the greater the reduction in intensity of the far light source compared to the near light source at the isobestic wavelength. Thus, the hematocrit may be calculated from the ratio Rh. For example, from the experimentally obtained results of FIG. 4B the relationship between Rh and hematocrit can be calculated using the following equation: Hematocrit (%)=11.25*Rh+15. In general, the hematocrit may be calculated as a polynomial function of Rh.

Calculation of Oxygen Saturation

Reflectance is defined as the ratio of the radiant energy reflected by a body to the energy incident upon it. The intensity of the light received by measurement light sensor 114 at each wavelength along the same path is dependent on the product of the reflectance of the blood at that wavelength and the intensity of the light emitted at that wavelength. By controlling, correcting or calibrating for variation in the light intensity emitted into the blood by each light source, as described above, and comparing the light intensity measured at each wavelength, the relative reflectance of the blood at each wavelength can be derived.

Host controller 360 comprises an oxygen saturation processing unit 366 for determining the oxygen saturation from measurement signal 314. The oxymetry sensor provides four calibrated intensity signals, one for each light source, to oxygen saturation processing unit 366. The intensity signals are $\lambda_1$, $\lambda_2$, $\lambda_3$ and $\lambda_{3\text{-far}}$) where $\lambda_1$ is the intensity signal at 670 nm, $\lambda_2$ is the intensity signal at 700 nm, $\lambda_3$ is the intensity signal at 805 nm and $\lambda_{3\text{-far}}$ is the intensity signal from the far 805 nm light source. The $\lambda_1$, $\lambda_2$, $\lambda_3$ signals can be used to generate two ratios R1=$\lambda_3/\lambda_2$ and R2=$\lambda_2/\lambda_1$. R1 is indicative of the relative reflectance of the blood for light of 805 nm compared to light of 700 nm. R2 is indicative of the relative reflectance of the blood for light of 700 nm compared to light of 670 nm.

FIG. 5A is a graph of experimentally obtained results plotting R1 against oxygen saturation. FIG. 5B is a graph of experimentally obtained results plotting R2 against oxygen saturation. The graphs of FIGS. 5A and 5B show plots of R1 and R2 against oxygen saturation at hematocrits of 0.25, 0.35 and 0.45. It can be observed from the graphs that each of the ratios R1 and R2 has an almost linear relationship to oxygen saturation at a given hematocrit. Each of the Ratios R1 and R2 can thus be used to calculate oxygen saturation. The advantage of using a ratio of light intensities rather than an absolute light intensity is that, if chosen correctly, both wavelengths will be affected relatively equally by factors other than oxygen saturation. This makes the ratio of light intensities far less sensitive to noise than absolute measurements. For example, the oxygen saturation can be calculated from the ratio R1 using the equation:

$$O_2^{R1} = m_{xo1}(R1 - R_{xo1}) + S_{xo1} \qquad \text{Equation 1.}$$

where $m_{xo1}$ is the slope of the plot of R1 against oxygen saturation and $R_{xo1}$ and $S_{xo1}$ are constants. Similarly, the oxygen saturation can also be calculated from the ratio R2 using the equation:

$$O_2^{R2} = m_{xo2}(R2 - R_{xo2}) + S_{xo2} \qquad \text{Equation 2.}$$

where $m_{xo2}$ is the slope of the plot of R2 against oxygen saturation and $R_{xo2}$ and $S_{xo2}$ are constants.

Figure 6:
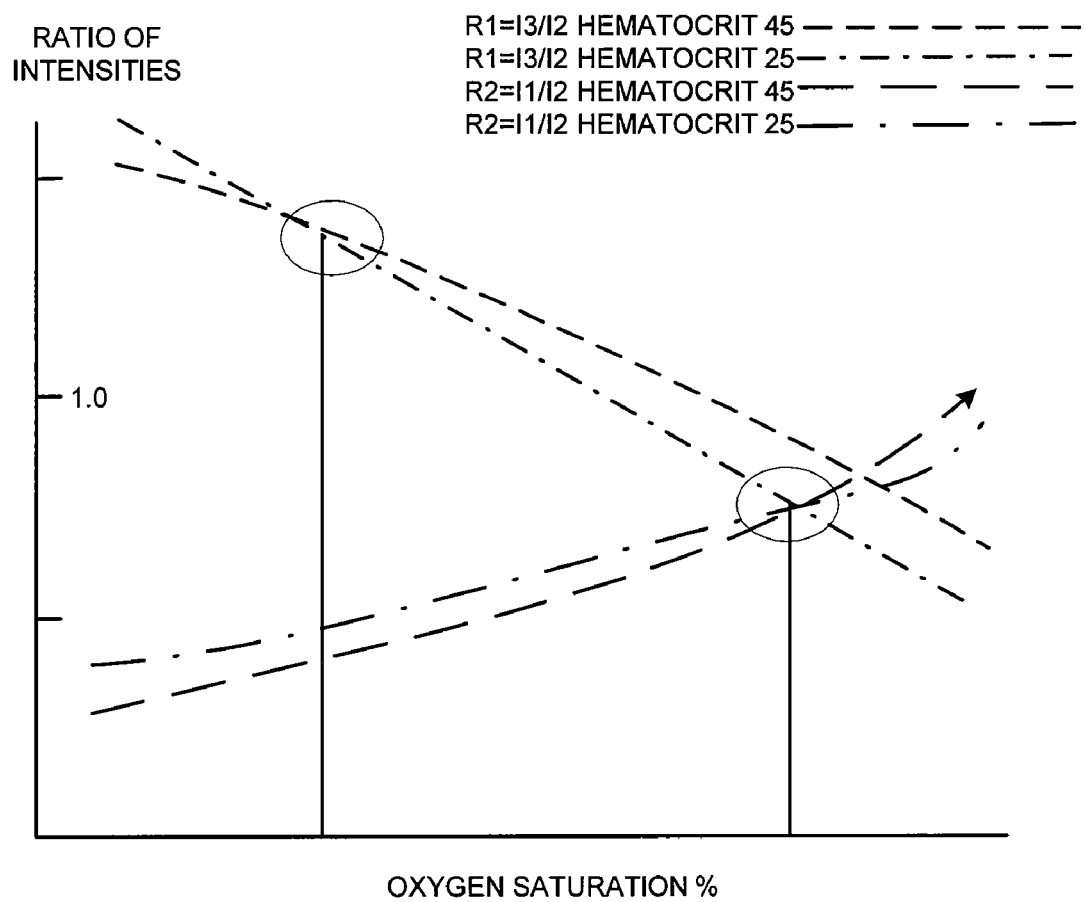
FIG. 6 illustrates a graph of the first and second light ratios against oxygen saturation at different levels of hematocrit.

However, as can be seen in FIGS. 4A and 4B the slope of each of R1 and R2 varies somewhat with hematocrit. Thus, if the slope is approximated by a constant, it is apparent from FIGS. 4A and 4B that the equations of Equations 1 and 2 will only approximate the correct oxygen saturation because the equations do not take hematocrit into account. One way of reducing the error in the approximation of oxygen saturation is to use both ratios R1 and R2 in weighted combination. As shown in FIG. 6, the ratio R1 shows the least variation with hematocrit at low oxygen saturations. In comparison, the ratio R2 shows least variation with hematocrit at high oxygen saturations. Thus, the two ratios can be used in combination to reduce the error in the calculation of oxygen saturation.

A general equation for combining the two oxygen saturation calculations is given by the equation:

$$O_2 = W_1 \times O_2^{R1} + W_2 \times O_2^{R2} \qquad \text{Equation 3.}$$

where $W_1$ and $W_2$ are weighting factors. The weighting factors $W_1$ and $W_2$ are variables selected, to give more weight to the value of the term derived from a particular ratio where that ratio is most accurate and least dependent upon hematocrit. One or other of $O_2^{R1}$ or $O_2^{R2}$ can be used as an estimate of oxygen saturation in order to determine the weighting factors $W_1$ and $W_2$. For example:

$$W_1 = \frac{O_2 R1}{100} \text{ or } W_1 = \frac{O_2 R2}{100}. \qquad \text{Equation 4.}$$

Note that $W_1$ is selected such that at low oxygen saturation (where R1 is most affected by hematocrit) the weighting $W_1$ for $O_2^{R1}$ is low and at high oxygen saturation (where R1 is least affected least by hematocrit) the weighting $W_1$ for $O_2^{R1}$ is high. The opposite weighting is provided for $W_2$. For example:

$$W_2 = 1 - \frac{O_2 R1}{100} \text{ or } W_2 = 1 - \frac{O_2 R2}{100}. \qquad \text{Equation 5}$$

$W_2$ is thus selected such that at low oxygen saturation (where R2 is least affected by hematocrit) the weighting $W_2$ for $0_2{}^{R2}$ is high and at high oxygen saturation (where R2 is most affected by hematocrit) the weighting $W_2$ for $0_2{}^{R2}$ is low. In this way, the two calculations of oxygen saturation based on the ratios R1 and R2 may be combined to yield a calculation of oxygen saturation that has less error than either of the calculations based on R1 or R2 alone. The result of such a weighted combination is relatively independent of variations in hematocrit.

The oxygen saturation can also be calculated from a combination of both ratios R1 and R2 using the following equations:

$$O_2 = \frac{A_0 + A_1 R1 + A_2 R2}{B_0 + B_1 R1 + B_2 R2}. \qquad \text{Equation 6}$$

$$O_2 = \frac{A_0 + A_1 R1 + A_2 R1^2 + A_3 R2}{B_0 + B_1 R1 + B_2 R1^2 + B_3 R2}. \qquad \text{Equation 7}$$

Where $A_0$, $A_1$, $A_2$, $A_3$, $B_0$, $B_1$, $B_2$ and $B_3$ are constants which can be selected empirically to provide the closest approximation between calculated and actual oxygen saturation.

Use of Hematocrit to Enhance Calculation of Oxygen Saturation

As indicated above, with respect to Equations 1 and 2, it is apparent from FIGS. 5A and 5B that the equations of Equations 1 and 2 will only approximate the correct oxygen saturation if m is approximated as a constant because the equations do not take hematocrit into account. One way to reduce the error, as previously described, is to combine the approximations from R1 and R2. A second way to reduce the error is to introduce a hematocrit term to correct for variation in hematocrit. For example, the slope m of the plot of oxygen saturation against the ratio R1 and R2 above depends on hematocrit and Rh is directly related to hematocrit. Thus, m can be written as a function of Rh using the linear (first order polynomial) equation:

$$m = (aRh + b) \qquad \text{Equation 8.}$$

or a second degree polynomial equation:

$$m = (aRh + bRh^2 + c) \qquad \text{Equation 9.}$$

where a, b and c are constants.

Figure 7:
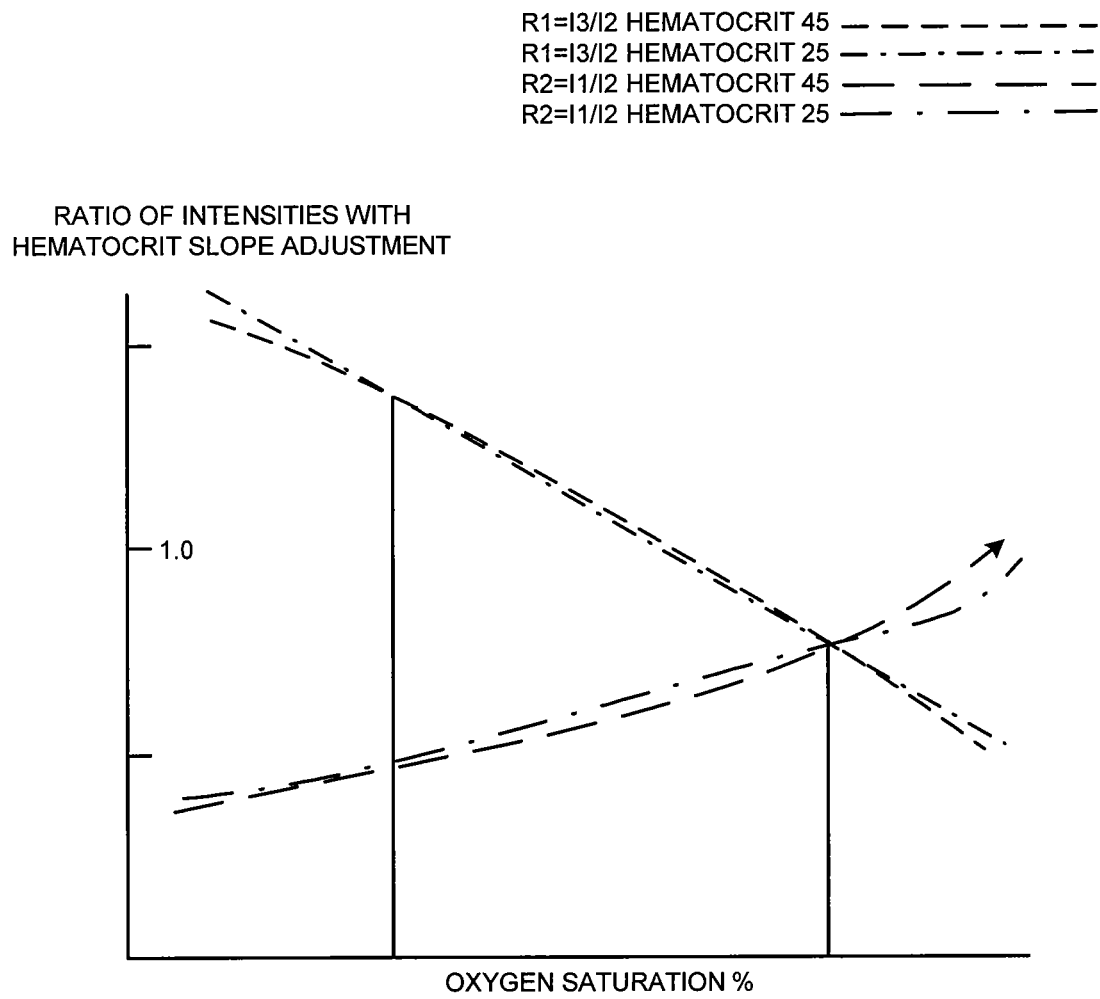
FIG. 7 illustrates a graph of the first and second light ratios against oxygen saturation at different levels of hematocrit after introduction of a hematocrit correction factor.

The calculation of oxygen saturation from each of the ratios R1 and R2 may be enhanced by incorporating the value of Rh using any of the following equations which substitute m (a hematocrit-dependent polynomial function of Rh) into Equation 8 and Equation 9 for $m_{xo1}$ and $m_{xo2}$ in Equations 1 and Equation 2 above.

$$O_2{}^{R1} = m(R1 - R_{xo1}) + S_{xo1} \qquad \text{Equation 10.}$$

$$O_2 R1 = m(R1 - R_{xo1}) + S_{xo1} \qquad \text{Equation 11.}$$

$$O_2{}^{R2} = m(R2 - R_{xo2}) + S_{xo2} \qquad \text{Equation 12.}$$

$$O_2{}^{R2} = m(R2 - R_{xo2}) + S_{xo2} \qquad \text{Equation 13.}$$

Where a, b, c, $R_{xo1}$, $S_{xo1}$, $R_{xo2}$, and $S_{xo2}$ are constants which can be solved empirically. These equations have the advantage that they take measured hematocrit into account. Thus, a more accurate calculation of oxygen saturation from each ratio, R1 and R2 is possible. FIG. 7 illustrates a simple example in which a simple slope correction is made to the plots of FIG. 6 to adjust for variation in hematocrit. Note that the plots of oxygen saturation against R1 and R2 corrected by Rh show much reduced variation with hematocrit. Furthermore oxygen saturation can be calculated from the combination of the ratios R1 and R2 by substituting the hematocrit-dependent term m for one or more coefficients of Equations 6 and 7 above. Such substitution yields equations for calculating oxygen saturation, including but not limited to the following:

$$O_2 = \frac{A_0 + mR1 + A_2 R2}{B_0 + B_1 R1 + B_2 R2}. \qquad \text{Equation 14}$$

$$O_2 = \frac{A_0 + A_1 R1 + A_2 R2}{B_0 + B_1 R1 + mR2}. \qquad \text{Equation 15}$$

$$O_2 = \frac{A_0 + mR1 + A_2 R2}{B_0 + mR1 + B_2 R2}. \qquad \text{Equation 16}$$

$$O_2 = \frac{A_0 + mR1 + A_2 R2}{B_0 + B_1 R1 + mR2}. \qquad \text{Equation 17}$$

$$O_2 = \frac{A_0 + mR1 + A_2 R1^2 + A_3 R2}{B_0 + B_1 R1 + B_2 R1^2 + B_3 R2}. \qquad \text{Equation 18}$$

$$O_2 = \frac{A_0 + A_1 R1 + A_2 R1^2 + A_3 R2}{B_0 + m_1 R1 + B_2 R1^2 + B_3 R2}. \qquad \text{Equation 19}$$

$$O_2 = \frac{A_0 + A_1 R1 + mR1^2 + A_3 R2}{B_0 + m_1 R1 + B_2 R1^2 + B_3 R2}. \qquad \text{Equation 20}$$

$$O_2 = \frac{A_0 + A_1 R1 + A_2 R1^2 + A_3 R2}{B_0 + B_1 R1 + mR1^2 + B_3 R2}. \qquad \text{Equation 21}$$

$$O_2 = \frac{A_0 + A_1 R1 + mR1^2 + A_3 R2}{B_0 + B_1 R1 + mR1^2 + B_3 R2}. \qquad \text{Equation 22}$$

$$O_2 = \frac{A_0 + A_1 R1 + mR1R2 + A_3 R2}{B_0 + B_1 R1 + B_2 R1R2 + B_3 R2}. \qquad \text{Equation 23}$$

$$O_2 = \frac{A_0 + A_1 R1 + A_2 R1R2 + A_3 R2}{B_0 + B_1 R1 + mR1R2 + B_3 R2}. \qquad \text{Equation 24}$$

$$O_2 = \frac{A_0 + mR1 + A_2 R1R2 + A_3 R2}{B_0 + B_1 R1 + B_2 R1R2 + mR2}. \qquad \text{Equation 25}$$

$$O_2 = \frac{A_0 + mR1 + mR1R2 + A_3 R2}{B_0 + B_1 R1 + mR1R2 + B_3 R2}. \qquad \text{Equation 26}$$

As described in equations 8 and 9, above, m can be calculated in each of equations 14 to 26 as a first, second or greater order polynomial function of Rh. The above equations are given as examples only. There are many alternative equations which may be used to derive oxygen saturation from R1 and R2. In each case, the calculation of oxygen saturation may be enhanced by utilizing the hematocrit-dependent term, m, which can be calculated using a polynomial function of the ratio Rh. The hematocrit term is used as a correction factor to compensate for the variation in the relationship between the ratio (R1 or R2) and oxygen saturation at different hematocrits. The resultant equations more closely approximate the true oxygen saturation and are not perturbed by variations in hematocrit.

Implantable Stimulation Device

The present invention is particularly useful as part of an implantable device such as an implantable stimulation device. FIG. 8 illustrates an exemplary implantable stimulation device 810 in electrical communication with a patient's heart 800 by way of four leads 820, 830, 840 and 850 suitable for multi-chamber sensing, stimulation and shock therapy. Implantable stimulation device 810 can be integrated with one of the embodiments of the oxymetry sensor 100 discussed above. That is, a common housing can be used to containing the elements of the oxymetry sensor (e.g., light sources 102, 104, 106, 108 and light sensor 112, 114, 116) and the elements of the implantable stimulation device 810. Alternatively, separate housings can be used to house the oxymetry sensor 100 and the stimulation device 810. Additionally, the stimulation device may communicate over a wireless link with external sensors such as PPG sensors incorporated into a finger cuff, a wristband, a configuration resembling a watch, or a configuration resembling a clip-on earring.

To sense atrial cardiac signals and to provide right atrial chamber stimulation therapy, implantable stimulation device 810 is coupled to an implantable right atrial lead 820 having at least an atrial tip electrode 822, which typically is implanted in the patient's right atrial appendage. In accordance with one embodiment of the present invention, right atrial lead 820 also comprises an oxymetry sensor 824 for measuring mixed-venous oxygen saturation.

To sense left atrial and ventricular cardiac signals and to provide left-chamber pacing therapy, implantable stimulation device 810 is coupled to a "coronary sinus" lead 840 designed for placement in the "coronary sinus region" 805 via the coronary sinus so as to place a distal electrode adjacent to the left ventricle 808 and additional electrode(s) adjacent to the left atrium 806. As used herein, the phrase "coronary sinus region" 805 refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 840 is designed to receive atrial and ventricular cardiac signals and to deliver left ventricular pacing therapy using at least a left ventricular tip electrode 842, left atrial pacing therapy using at least a left atrial ring electrode 844, and shocking therapy using at least a left atrial coil electrode 846.

Implantable stimulation device 810 is also shown in communication with the patient's heart 800 by way of an implantable left atrial lead 850 having in this embodiment, a left atrial sensor 852 implanted in the septum 803 between the right atrium 802 and left atrium 806. Left atrial sensor 852 is in one embodiment comprises a hermetically-sealed pressure transducer module. In one embodiment, the implantable module comprises a proximal anchor and a distal anchor which are configured to sandwich an atrial septum wall 803 (or the left atrial free wall, the pulmonary vein wall, or any other suitable wall of a heart or a blood vessel) between the proximal anchor leg and the distal anchor leg and to support the module in the septum wall 803. In one embodiment, the sensor module comprises one or more sensors in addition to a pressure transducer at its distal end. These sensors may include a plurality of pressure transducers to measure pressures in the transmural space or locations proximal to the transmural space, or to measure differential pressure between the distal diaphragm and another location. Other types of sensors include, but are not limited to, temperature sensors, electrodes for measuring electrical activity, and oxymetry sensors. In one embodiment, the sensor module contains at least one electrode for stimulating the organ in which it is placed. For example, such an electrode or electrodes may be used for electrically pacing the left atrium. A suitable embodiment of a lead-mounted left atrial sensor is the Savacor HEARTPOD™ which in the present application is connected via lead 850 to implantable stimulation device 810. Details of such left atrial sensor modules may be found in U.S. patent application Ser. No. 11/115,991 entitled, "Implantable Pressure Transducer System Optimized For Anchoring And Positioning" filed Apr. 27, 2005 to Eigler et al.; Ser. No. 10/270,784 entitled "Permanently Implantable System And Method For Detecting, Diagnosing And Treating Congestive Heart Failure" filed: Oct. 11, 2002 to Eigler et al.; and Ser. No. 11/027,598 entitled "Flexible Lead For Digital Cardiac Rhythm Management" filed: Dec. 30, 2004 to Mann et al. all of which are incorporated herein by reference.

Implantable stimulation device 810 is also shown in electrical communication with the patient's heart 800 by way of an implantable right ventricular lead 830 having, in this embodiment, a right ventricular tip electrode 832, a right ventricular ring electrode 834, a right ventricular blood-glucose concentration coil electrode 836, and an SVC coil electrode 838. Typically, the right ventricular lead 830 is transvenously inserted into the heart 800 so as to place the right ventricular tip electrode 832 in the right ventricular apex so that the right ventricular coil electrode 836 will be positioned in the right ventricle and the SVC coil electrode 838 will be positioned in the superior vena cava. Accordingly, the right ventricular lead 830 is capable of receiving cardiac signals, and delivering stimulation in the form of pacing and shock therapy to the right ventricle. In accordance with one embodiment of the present invention, the time-varying impedance between an electrode in the right ventricle and the housing 812 of implantable stimulation device 810 is used to calculate cardiac stroke volume.

FIG. 9 illustrates a simplified block diagram of the multi-chamber implantable stimulation device 810 which is capable of measuring blood-oxygen saturation and treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of measuring blood-oxygen saturation with or without treating the heart with cardioversion, defibrillation and/or pacing stimulation.

Referring again to FIG. 9, implantable stimulation device 810 includes a housing 812 which is often referred to as a "can", "case" or "case electrode", and which may be programmably selected to act as the return electrode for all "unipolar" modes. Housing 812 may further be used as a return electrode alone or in combination with one or more of the coil electrodes 836, 838 or 846, for shocking purposes. Housing 812 further includes a connector (not shown) having a plurality of terminals, 942, 943, 944, 945, 946, 947, 948, 949, 952, 954, 956, and 958 (shown schematically and, for convenience, the names of the electrodes or sensors to which they are connected are shown next to the terminals). To achieve right atrial sensing and pacing, the connector includes at least a right atrial tip terminal 942 adapted for connection to the right atrial tip electrode 822 ($A_R$TIP), an oxymetry sensor terminal 943 adapted for connection to the oxymetry sensor 824 (OXY.) To achieve left chamber sensing, pacing and/or shocking, the connector includes at least a left ventricular tip terminal 944, a left atrial sensor terminal 945, a left atrial ring terminal 946, and a left atrial shocking terminal 947, which are adapted for connection to the left ventricular tip electrode 842 ($V_L$TIP), the left atrial sensor 852 ($A_L$SENS.), the left atrial ring electrode 844 ($A_L$RING), and the left atrial coil electrode 846 ($A_L$COIL), respectively. To support right chamber sensing, pacing and/or shocking, the connector further includes a right ventricular tip terminal 952, a right ventricular ring terminal 954, a right ventricular shocking terminal 956, and a superior vena cava terminal 958, which are adapted for connection to the right ventricular tip electrode 832 ($V_R$TIP), right ventricular ring electrode 834 ($V_R$RING), the right ventricular coil electrode 836 ($V_R$COIL), and the superior vena cava coil electrode 838 (SVC), respectively. The connector may also include one or more I/O terminals 948, 949 for communicating with optional implantable devices external to housing 812.

At the core of implantable stimulation device 810 is a programmable host controller 960 which controls the various modes of stimulation therapy and performs calculations of blood-oxygen saturation. As is well known in the art, host controller 960 may be a microcontroller and typically includes a microprocessor or equivalent control circuitry or processor, designed specifically for controlling the delivery of stimulation therapy, and may further include RAM or ROM memory, logic and timing circuitry, state machine circuitry, and I/O circuitry. Typically, host controller 960 includes the ability to process or monitor input signals (data) as controlled by program code stored in a designated block of memory. Host controller 960 includes the ability to calculate blood-oxygen saturation from measured oximetry sensor data and stored parameters. The details of the design and operation of host controller 960 are not critical to the present invention. Rather, any suitable host controller 960 may be used that carries out the functions described herein. The use of microprocessor-based control circuits for performing timing and data analysis functions is well known in the art.

As shown in FIG. 9, an atrial pulse generator 970 and a ventricular pulse generator 972 generate pacing stimulation pulses for delivery by right atrial lead 820, right ventricular lead 830, and/or coronary sinus lead 840 via a switch bank 920. It is understood that in order to provide stimulation therapy in each of the four chambers of the heart, atrial pulse generator 970 and ventricular pulse generator 972 may include dedicated, independent pulse generators, multiplexed pulse generators, or shared pulse generators. Atrial pulse generator 970 and ventricular pulse generator 972 are controlled by host controller 960 via appropriate control signals 976 and 978, respectively, to trigger or inhibit the stimulation pulses.

Host controller 960 further includes pacing control circuitry 962 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

Implantable stimulation device 810 may operate as an implantable cardioverter/defibrillator (ICD) device. That is, it may detect the occurrence of an arrhythmia, and automatically apply an appropriate electrical shock therapy to the heart aimed at terminating the detected arrhythmia. To this end, host controller 960 further controls a shocking circuit 973 by way of a control signal 974. The shocking circuit 973 generates shocking pulses of low (up to 0.5 joules), moderate (0.5-10 joules), or high (11-40 joules) energy, as controlled by the host controller 960. Such shocking pulses are applied to the patient's heart through at least two shocking electrodes, as shown in this embodiment, selected from left atrial coil electrode 846, right ventricular coil electrode 836, and/or SVC coil electrode 838. As noted above, housing 812 may act as an active electrode in combination with the right ventricular electrode 836, or as part of a split electrical vector using SVC coil electrode 838 or left atrial coil electrode 846 (e.g., using the right ventricular electrode as a common electrode).

Switch bank 920 includes a plurality of electrically-configurable switches for connecting the desired electrodes to the appropriate I/O circuits, thereby providing complete electrode programmability. Accordingly, switch bank 920, in response to a control signal 980 from host controller 960, determines the polarity of the stimulation pulses (e.g., unipolar, bipolar, combipolar, etc.) by selectively closing the appropriate combination of switches (not shown) as is known in the art. If multiple right ventricular electrodes are employed to generate a single averaged ventricular signal, then switch bank 920 is configured to allow the paralleling (or averaging) of the multiple right ventricular electrodes to simulate a large electrode for accurate sensing of the T-wave.

Atrial sensing circuits 982 and ventricular sensing circuits 984 may also be selectively coupled to right atrial lead 820, coronary sinus lead 840, and right ventricular lead 830, through the switch bank 920, for detecting the presence of cardiac activity in each of the four chambers of the heart. Accordingly, the atrial and ventricular sensing circuits 982 and 984 may include dedicated sense amplifiers, multiplexed amplifiers, or shared amplifiers. Switch bank 920 determines the "sensing polarity" of the cardiac signal by selectively closing the appropriate switches. In this way, the clinician may program the sensing polarity independent of the stimulation polarity.

Each of the sensing circuits, 982 and 984, preferably employ one or more low power, precision amplifiers with programmable gain and/or automatic gain control, bandpass filtering, and a threshold detection circuit, to selectively sense the cardiac signal of interest. The automatic gain control enables implantable stimulation device 810 to deal effectively with the difficult problem of sensing the low amplitude signal characteristics of atrial or ventricular fibrillation.

The outputs of the atrial and ventricular sensing circuits 982 and 984 are connected to host controller 960 for triggering or inhibiting the atrial and ventricular pulse generators 970 and 972, respectively, in a demand fashion, in response to the absence or presence of cardiac activity, respectively, in the appropriate chambers of the heart. The atrial and ventricular sensing circuits 982 and 984, in turn, receive control signals over signal lines 986 and 988 from host controller 960, for controlling the gain, threshold, polarization charge removal circuitry (not shown), and the timing of any blocking circuitry (not shown) coupled to the inputs of the atrial and ventricular sensing circuits 982 and 984.

For arrhythmia detection, implantable stimulation device 810 utilizes the atrial and ventricular sensing circuits 982 and 984 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the host controller 960 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition unit 990. Data acquisition unit 990 is configured to acquire intracardiac electrogram signals, convert the raw analog data into digital signals, and store the digital signals for later processing and/or telemetric transmission to an external device 902. Data acquisition unit 990 is coupled to right atrial lead 820, the coronary sinus lead 840, the right ventricular lead 830, and the left atrial lead 850 through the switch bank 920 to sample cardiac signals across any pair of desired electrodes.

Capture occurs when an electrical stimulus applied to the heart is of sufficient energy to depolarize the cardiac tissue, thereby causing the heart muscle to contract. Advantageously, data acquisition unit 990 may be coupled to host controller 960 or other detection circuitry, for detecting an evoked response from the heart 800 in response to an applied stimulus, thereby aiding in the detection of "capture". Host controller 960 detects a depolarization signal during a window following a stimulation pulse, the presence of which indicates that capture has occurred. Host controller 960 enables capture detection by triggering the ventricular pulse generator 972 to generate a stimulation pulse, starting a capture detection window using the timing circuitry within host controller 960. Host controller 960 enables data acquisition unit 990 via control signal 992 to sample the cardiac signal that falls in the capture detection window and, based on the amplitude of the sampled cardiac signal, determines if capture has occurred. The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection unit used is not critical to the present invention.

Implantable stimulation device 810 may also include one or more host sensors 930, which can be located in or on the housing 812 of implantable stimulation device 810 as shown, or can be located adjacent to the housing. These sensors can include, by way of example, motion sensors, blood flow sensors, temperature sensors, oxymetry sensors and blood pressure sensors. Host sensors 930 may include a physiologic sensor 932, a temperature sensor 934 and an oxymetry sensor 936. As shown in FIG. 9, host sensors 930 may be connected to via switch bank 920 to host controller 960 directly or through data acquisition unit 990 such that host controller 960 can receive measurements of physiological variables from the host sensors 930.

Physiologic sensor 932 is commonly referred to as a "rate-responsive" sensor because it is typically used to adjust pacing stimulation rate according to the exercise state of the patient. However, the rate-responsive sensor may also be used to detect changes in cardiac output, changes in the physiological condition of the heart, or diurnal changes in activity (e.g., detecting sleep and wake states). Accordingly, host controller 960 responds to the rate-responsive sensor by adjusting the various pacing parameters (such as rate, AV Delay, V-V Delay, etc.) at which the atrial and ventricular pulse generators, 970 and 972, generate stimulation pulses.

Temperature sensor 934 may comprise any electronic device for measuring temperature. Suitable devices include, but are not limited to, thermopiles, thermistors, thermocouples. Thermopiles measure temperature by measuring IR radiation incident of the detector surface. Thus, if a thermopile is used as temperature sensor 934, a window transparent to IR (not shown) must be provided to allow heat/IR radiation from the blood to fall on the surface of the detector. Thermistors and thermocouples may measure temperature by conduction. Such temperature measuring devices should therefore be placed in good thermal contact with the blood. As shown in FIG. 9, temperature sensor 934 may be placed in contact with housing 812 of implantable stimulation device 810. Housing 812 is preferably made of metal. As housing 812 is in good thermal contact with the tissues surrounding the housing and also with temperature sensor 934, and because metal is a good conductor of heat, temperature sensor 934 can accurately measure the temperature of the body at the location where implantable stimulation device 810 has been implanted. Preferably implantable stimulation device 810 is implanted in the subclavian pocket and thus temperature sensor 934 measures the temperature of the body in the subclavian pocket. This temperature will vary based on such factors as external temperature and activity of the subject.

As further shown in FIG. 9, implantable stimulation device 810 comprises an impedance measuring circuit 996 which is enabled by host controller 960 via a control signal 997. Certain applications for an impedance measuring circuit 996 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds and/or monitoring pulmonary edema; detecting when the device has been implanted; measuring stroke volume; and detecting the opening of the valves, etc. Impedance measuring circuit 996 is advantageously coupled to the switch bank 920 so that any desired electrode may be used. Data from impedance measuring circuit 996 may also be used by host controller 960 to assess cardiac output.

Host controller 960 is also coupled to a memory 916 by a suitable data/address bus 913. Memory 916 stores the programmable operating parameters used by the host controller 960 in order to customize the operation of implantable stimulation device 810 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 800 within each respective tier of therapy. A feature of implantable stimulation device 810 is the ability to receive and store a relatively large amount of data (e.g., from data acquisition unit 990), which may then be used for subsequent analysis to guide the programming of implantable stimulation device 810.

Advantageously, the operating parameters of the implantable device 810 may be non-invasively programmed into the memory 916 through a telemetry circuit 901 in telemetric communication with an external programmer 902, such as a, transtelephonic transceiver, or a diagnostic system analyzer. The telemetry circuit 901 is activated by the host controller by a control signal 906. The telemetry circuit 901 advantageously allows intracardiac electrograms, blood-oxygen saturation levels, temperature data, hematocrit information, stroke volume, heart-rate, other measured physiological variable and status information relating to the operation of the implantable stimulation device 810 (as contained in the host controller 960 or memory 916) to be sent to an external device such as programmer 902, reader 903, or portable device 904 through an established communication link 905. Typically communication link 905 can only operate between telemetry circuit 901 and one of programmer 902, reader 903, or portable device 904 at any one time. A "handshake" signal sent from the external device may be used to identify the particular device with which the telemetry circuit 901 is in communication thereby defining what operations may be performed by the device. For example, programming of implantable stimulation device 810 will preferably only be permitted by programmer 902 under the control of a physician.

Implantable stimulation device 810 further includes initiation circuit 908. Initiation circuit 908 may comprise magnet detection circuitry. Initiation circuit 908 is coupled to host controller 960 by connection 909 and/or to telemetry circuit 901 by connection 910. The purpose of the initiation circuit is to detect an initiation signal from outside the patient. For example, a magnet placed over the cardiac implantable stimulation device 810 may be used as the initiation signal. The magnet may be used by a clinician to perform various test functions of the cardiac implantable stimulation device 810 and/or to signal host controller 960 that an external programmer 902 is in place to receive or transmit data to host controller 960 through the telemetry circuit 901. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (note: this relates to transfer of EGM data) (McClure et al.), which patents are hereby incorporated herein by reference.

A drug pump 907 may be provided, in the housing 812 or attached to the housing. Such drug pumps may be used to supply insulin. Blood-glucose analysis unit 968 transmits control signals to insulin pump 907 for adjusting the amount of insulin delivered to the patient in response to the current blood-oxygen saturation. Information regarding implantable insulin pumps may be found in U.S. Pat. No. 4,731,051 to Fischell and in U.S. Pat. No. 4,947,845 to Davis, both of which are incorporated by reference herein. The insulin pumps discussed therein, or other suitable insulin pumps, are modified as needed to permit receipt of control signals from host controller 960.

Implantable stimulation device 810 additionally includes a power source such as a battery 914 which provides operating power to all the circuits of implantable stimulation device 810. For implantable stimulation device 810, which employs shocking therapy, battery 914 must be capable of operating at low current drains for long periods of time and also be capable of providing high-current pulses (for charging capacitor 912) when the patient requires a shock pulse. Battery 914 preferably has a predictable discharge characteristic so that elective replacement time can be detected. Accordingly, implantable stimulation device 810 can employ lithium/silver vanadium oxide batteries.

Oxymetry sensors 936 and 824 comprise photoplethysmography/oxymetry sensors such as shown in FIGS. 1A and 1B. Oxymetry sensors 936, 824 may be used to measure blood-oxygen saturation in the tissues adjacent to the sensor. Implantable stimulation device 810 may be implanted in the subclavian pocket and thus oxymetry sensor 936 may be used to measure the blood-oxygen saturation level in the tissues of the subclavian pocket using pulse oximetry techniques as described in more detail above. The oxygen saturation level in the tissues of the subclavian pocket as measured by oxymetry sensor 936 can be used as a measure of arterial oxygen saturation. Oxymetry sensor 824 may be implanted in the right atrium or right ventricle where it measures the oxygen saturation of mixed venous blood. The measurements of arterial oxygen saturation may be compared or combined with measurements of mixed venous oxygen saturation obtained to provide more detailed analysis of oxygen metabolism. For example, the rate at which oxygen is being consumed by the body can be determined using the difference between arterial oxygen saturation and venous oxygen saturation combined with the cardiac output using the Fick equation. The rate of oxygen consumption provides a measure of the activity level of the subject and also the rate of glucose consumption. Information regarding the rate of oxygen consumption may be used by the implantable stimulation device to modulate the electrical stimulation of the heart so that it is appropriate for the patient's level of activity.

In one embodiment of the invention, host controller 960 comprises an oxymetry processing unit 964. Oxymetry processing unit 964 receives oxymetry data from the outputs of one or both of oxymetry sensor 824 (See FIG. 8) and oxymetry sensor 936 (See FIG. 9). Oxymetry processing unit 964 then performs some or all of the functions of calibration processing unit 362, hematocrit processing unit 364 and oxygen saturation processing unit 366 of FIG. 3.

In one embodiment, the oxymetry data received by oxymetry processing unit 964 includes four digitized intensity signals, one for each light source of oxymetry sensor 100 as shown in FIG. 1A. The intensity signals are $\lambda_1$, $\lambda_2$, $\lambda_3$ and $\lambda_{3\text{-}far}$ where $\lambda_1$ represents the intensity at 670 nm, $\lambda_2$ represents the intensity at 700 nm, $\lambda_3$ represents the intensity at 805 nm and $\lambda_{3\text{-}far}$ represents the intensity from the far 805 nm light source. Oxymetry processing unit 964 utilizes the $\lambda_1$, $\lambda_2$, $\lambda_3$ signals to generate the two ratios $R1=\lambda_3/\lambda_2$ and $R2=\lambda_2/\lambda_1$. Oxymetry processing unit 964 utilizes the $\lambda_3$ and $\lambda_{3\text{-}far}$ far signals to generate the ratio $Rh=\lambda_3/\lambda_{3\text{-}far}$. Oxymetry processing unit then calculates m as a polynomial function of Rh. Oxymetry processing unit 964 then utilizes the ratios R1, R2 and the hematocrit-dependent term m to calculate blood-oxygen saturation. In particular embodiments of the present invention, oxymetry processing unit 964 may utilize one of the equations 10-26 to calculate blood-oxygen saturation from the ratios R1, R2 and Rh as described above.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A method for determining a value of oxygen saturation of blood, comprising:
    (a) determining a value R1 indicative of a relative reflectance of the blood for light of a first wavelength compared to light of a second wavelength, and determining a value R2 indicative of a relative reflectance of the blood for light of the second wavelength compared to light of a third wavelength;
    (b) determining a value m indicative of a level of hematocrit of the blood; and
    (c) determining a value of oxygen saturation of the blood utilizing a first polynomial function of the values R1 and R2 divided by a second polynomial function of the values R1 and R2, wherein one of the first and second polynomial functions of the values R1 and R2 includes the value m as a factor;

wherein at least one of steps (a), (b) and (c) is performed using at least one processor.

2. The method of claim 1, wherein step (a) includes:
(a.1) transmitting light of the first wavelength toward the blood;
(a.2) transmitting light of the second wavelength toward the blood;
(a.3) detecting an intensity of light of the first wavelength that is reflected by the blood;
(a.4) detecting an intensity of light of the second wavelength that is reflected by the blood; and
(a.5) determining the value R1 utilizing the intensities detected at (a.3) and (a.4).

3. The method of claim 2, wherein step (a.2) comprises detecting an intensity of light of the first wavelength that is reflected by the blood over a first distance, and step (b) comprises:
(b1) detecting an intensity of light of the first wavelength that is reflected by the blood over a second distance, longer than the first distance;
(b.2) determining a ratio Rh of the intensities detected at (a.2) and (b.1); and
(b.3) determining the value m as a function of the ratio Rh.

4. The method of claim 1, wherein step (b) comprises:
(b.1) transmitting light of the first wavelength toward the blood;
(b.2) detecting an intensity of light of the first wavelength that is reflected by the blood over a first distance;
(b.3) detecting an intensity of light of the first wavelength that is reflected by the blood over a second distance, longer than the first distance;
(b.4) determining a ratio Rh of the intensities detected at (b.2) and (b.3); and
(b.5) determining the value m as a function of the ratio Rh.

5. The method of claim 4, wherein step (b.5) comprises determining the value m as a first-order polynomial function of the ratio Rh.

6. The method of claim 4, wherein step (b.5) comprises determining the value m as a second-order polynomial function of the ratio Rh.

7. The method of claim 3, wherein:
the first wavelength is 805 nm.

8. The method of claim 1, wherein the first polynomial function of the values R1 and R2 is a first order polynomial function, and the second polynomial function of the values R1 and R2 is a first order polynomial function.

9. The method of claim 4, wherein the first polynomial function of the values R1 and R2 is a second order polynomial function, and the second polynomial function of the values R1 and R2 is a second order polynomial function.

10. The method of claim 9, wherein at least one of the first second-order polynomial function of the values R1 and R2 and the second second-order polynomial function of the values R1 and R2 includes the value m as a factor, wherein the value m is one of a first-order and second-order polynomial function of the ratio Rh.

11. A method for determining a value of oxygen saturation of blood, comprising:
(a) emitting light of first, second and third wavelengths toward the blood;
(b) generating light intensity values indicative of the intensity of light of each of the first, second and third wavelengths reflected back from the blood over a first distance;

(c) using the light intensity values to determine a value R1 indicative of a relative reflectance of the blood for light of the third wavelength compared to light of the second wavelength;
(d) using the light intensity values to determine a value R2 indicative of a relative reflectance of the blood for light of the second wavelength compared to light of the first wavelength;
(e) determining a value m indicative of a level of hematocrit of the blood; and (f) determining a value of oxygen saturation of the blood utilizing a polynomial function of the values R1, R2 and m.

12. The method of claim 11, further comprising:
generating a light intensity value indicative of the intensity of light of the third wavelength reflected back from the blood over a second distance different than the first distance; and
wherein step (e) comprises determining the ratio Rh indicative of hematocrit based on comparing the reflectance of the blood for light of the third wavelength measured over the first distance to the reflectance of the blood for light of the third wavelength measured over the second distance, and determining the value m as a polynomial function of the ratio Rh.

13. An implantable system for measuring oxygen saturation of blood comprising:
a plurality of light sources that emit light into the blood at first, second, and third wavelengths;
one or more light sensors that permit the measurement of the relative reflectance of the blood for light of each of the first, second, and third wavelengths;
a hematocrit calculation unit that calculates a ratio Rh of relative reflectance of the blood for light of the third wavelength over a first distance relative to a second longer distance, wherein the ratio Rh is indicative of a level of hematocrit of the blood; and
an oxygen saturation calculation unit that calculates a value R1 indicative of relative reflectance of the blood for light of the third wavelength relative to light of the second wavelength, and calculates a value R2 indicative of relative reflectance of the blood for light of the second wavelength relative to light of the first wavelength, and determines the oxygen saturation of the blood based on a first polynomial function of the values R1 and R2 divided by a second polynomial function of the values R1 and R2, wherein one of the first and second polynomial functions of the values R1 and R2 includes a third polynomial function of the ratio Rh as a factor.

14. The implantable system of claim 13, wherein the first polynomial function is a second order polynomial function, and the second polynomial function is a second order function.

15. The implantable system of claim 13, wherein the third wavelength of light is isobestic with respect to oxygenated and deoxygenated blood.

16. The system of claim 13, wherein the first polynomial function of the values R1 and R2 is a first order polynomial function, and the second polynomial function of the values R1 and R2 is a first order polynomial function.

17. The system of claim 13, wherein the first polynomial function of the values R1 and R2 is a second order polynomial function, and the second polynomial function of the values R1 and R2 is a second order polynomial function.

18. The system of claim 13, wherein the third wavelength is 805 nm.

19. A method for determining oxygen saturation of blood having hematocrit, comprising:

(a) measuring a first property of the blood that varies with the oxygen saturation of the blood and the hematocrit of the blood and generating a value R1 indicative of the first property;

(b) measuring a second property of the blood that varies with the oxygen saturation of the blood and the hematocrit of the blood and generating a value R2 indicative of the second property;

(c) measuring a third property of the blood that varies with the hematocrit of the blood but that does not vary significantly with the oxygen saturation and generating a ratio Rh indicative of the third property; and (d) determining the oxygen saturation of the blood utilizing a first polynomial function of the values R1 and R2 divided by a second polynomial function of the values R1 and R2, wherein one of the first and second polynomial functions of the values R1 and R2 includes a third polynomial function of the ratio Rh as a factor;

wherein at least step (d) is performed using at least one processor.

20. The method of claim 19, wherein the first property is one of: relative transmittance of the blood for light of first and second different wavelengths; relative absorbance of the blood for light of first and second different wavelengths; and relative reflectance of the blood for light of first and second different wavelengths.

21. The method of claim 19, wherein the third property is relative reflectance of the blood for light of a selected wavelength measured over a first distance and a second distance longer than the first distance.

22. The method of claim 21, wherein the selected wavelength is a wavelength selected such that the reflectance of the blood for light of the selected wavelength is substantially the same for oxygenated and deoxygenated blood.

23. The method of claim 22, wherein the selected wavelength is 805 nm.

24. The method of claim 19, wherein the first polynomial function of the values R1 and R2 is a first order polynomial function, and the second polynomial function of the values R1 and R2 is a first order polynomial function.

* * * * *